United States Patent
Bertini et al.

(10) Patent No.: US 10,883,347 B2
(45) Date of Patent: Jan. 5, 2021

(54) METHODS AND SYSTEMS FOR DETECTING MANHOLE EVENTS

(71) Applicant: Novinium, Inc., Kent, WA (US)

(72) Inventors: Glen John Bertini, Fox Island, WA (US); David C. Busby, Midland, MI (US); Weston Philips Chapin Ford, Seattle, WA (US); Jeffrey Andrew Thomas, Kent, WA (US)

(73) Assignee: NOVINIUM, INC., Kent, WA (US)

( * ) Notice: Subject to any disclaimer, the term of this patent is extended or adjusted under 35 U.S.C. 154(b) by 0 days.

(21) Appl. No.: 16/208,098

(22) Filed: Dec. 3, 2018

(65) Prior Publication Data

US 2020/0173262 A1     Jun. 4, 2020

(51) Int. Cl.
| | |
|---|---|
| E02D 27/00 | (2006.01) |
| F24F 11/00 | (2018.01) |
| F24F 13/02 | (2006.01) |
| F24F 1/0073 | (2019.01) |
| E21B 43/12 | (2006.01) |
| E21B 21/08 | (2006.01) |
| E21B 34/08 | (2006.01) |
| E21B 47/06 | (2012.01) |

(52) U.S. Cl.
CPC ............ *E21B 43/12* (2013.01); *E21B 21/08* (2013.01); *E21B 34/08* (2013.01); *E21B 47/06* (2013.01)

(58) Field of Classification Search
None
See application file for complete search history.

(56) References Cited

U.S. PATENT DOCUMENTS

| | | | |
|---|---|---|---|
| 3,434,502 A | 3/1969 | Snelling | |
| 3,610,524 A | 10/1971 | Wallen | |
| 3,731,448 A | 5/1973 | Leo | |
| 4,513,205 A | 4/1985 | Splinter | |
| 5,301,959 A | 4/1994 | Gould | |
| 5,791,098 A | 8/1998 | Thomas | |
| 7,598,858 B2* | 10/2009 | Quist | G08B 21/12 |
| | | | 340/531 |
| 8,013,303 B2 | 9/2011 | Ershov et al. | |
| 9,961,418 B2* | 5/2018 | Rodriguez, Jr. | H04L 63/0428 |
| 2016/0356521 A1 | 12/2016 | Bertini et al. | |
| 2016/0356522 A1 | 12/2016 | Bertini et al. | |

(Continued)

OTHER PUBLICATIONS

Non-Final Office Action, dated Sep. 19, 2019, received in U.S. Appl. No. 16/208,120.

(Continued)

*Primary Examiner* — James G Sayre
*Assistant Examiner* — Douglas S Wood
(74) *Attorney, Agent, or Firm* — Davis Wright Tremaine LLP; George C. Rondeau, Jr.; Heather M. Colburn

(57) ABSTRACT

A system for use with a connection comprising a terminus opening into an underground vault. The system includes a perturbation detector and a system controller. The perturbation detector is configured to detect values of each of one or more properties and transmit a signal encoding the values to the system controller. The system controller is configured to receive the signal, use at least one of the values to determine whether a fire is occurring or has occurred, and alert a user when the system controller determines that the fire is occurring or has occurred.

18 Claims, 7 Drawing Sheets

(56) References Cited

U.S. PATENT DOCUMENTS

2017/0284689 A1 10/2017 Steele et al.

OTHER PUBLICATIONS

Zhang, Boggs and Murray, "Effect of Limiting Airflow in Mitigating Combustion-Driven Manhole Events," IEEE Electrical Insulation Magazine, vol. 27, No. 6, 2011.
Information Disclosure Statement Transmittal filed herewith.
Final Office Action, dated Feb. 6, 2020, received in U.S. Appl. No. 16/208,120.
International Search Report and Written Opinion, dated Feb. 5, 2020, received in International Application No. PCT/US2019/057050.

* cited by examiner

METHODS AND SYSTEMS FOR DETECTING MANHOLE EVENTS

BACKGROUND OF THE INVENTION

Field of the Invention

The present invention is directed generally to methods and systems for detecting manhole events.

Description of the Related Art

Network Fires and Explosions

Referring to FIG. 1, underground manhole systems are networks of nodes or vaults with at least one connection between adjacent nodes. FIG. 1 illustrates an exemplary underground manhole system 100 that includes a plurality of vaults 102 interconnected by a plurality of ducts or connections 104. In the example illustrated, the vaults 102 include vaults A-1, A-2, A-3, B-1, B-2, B-3, C-1, C-2, and C-3. Typically, the vaults 102 are spaced apart by approximately one city block and dozens of connections run between adjacent vaults. The connections 104 may be implemented as pipes carrying natural gas, steam, or other fluids. Alternatively, the connections 104 may be cables carrying power or communication signals. Over 90% of the equipment in these network systems is located in the connections and less than 10% of the equipment is located within one of the vaults. Unfortunately, these underground manhole systems are prone to fires and explosions. For example, a connection BB12 is illustrated as including a fire.

Accessing vaults in busy urban areas is not a trivial undertaking. Often busy city traffic must be disrupted. Notwithstanding the inconvenience, it is possible to inspect the 10% of the equipment in the vault. The 90% of the equipment (e.g., power cable, communication cables, etc.) located in the connections (e.g., connections 104) is not directly accessible via the vaults (e.g., vaults 102). Most often, when pieces of equipment located in a connection require replacement, the equipment can be pulled from the connection (e.g., a duct) and replaced with new equipment.

As a practical matter, there is no way to inspect cables located in the connections (e.g., ducts). FIG. 2 illustrates the connection BB12 housing an exemplary four-wire configuration 200 of the type most often used in secondary electrical networks. While the four-wire configuration 200 illustrated includes four cables in the single connection BB12 (e.g., duct), other numbers of cables and configurations are common. The configuration 200 includes cables Phase A, Phase B, Phase C, and Neutral. The cables Phase A, Phase B, and Phase C each include a copper or aluminum conductor (not shown) covered in one or more polymeric or elastomeric insulation and jacketing material 206. The cables Phase A, Phase B, and Phase C may be referred to as "phase cables." The cable Neutral may be a bare conductor (generally, copper or tin-plated-copper) or a covered conductor similar to the three phase cables Phase A, Phase B, and Phase C. Non-limiting examples of insulation and jacketing materials include styrene-butadiene rubber ("SBR"), neoprene, ethylene-propylene rubber ("EPR"), and polyethylene. Some have tried to inspect cables using snake-like robots, with little success because the majority of the cable surfaces lie against one another and against the bottom of the connection, which hides them from robotic inspection. U.S. patent application Ser. No. 16/190,832, filed Nov. 14, 2018, and titled "Methods of Using Component Mass Balance to Evaluate Manhole Events," describes methods and systems for sensing when fire or flammable gas accumulation occurs in duct-manhole systems (like the system 100). It turns out that small fires (such as smoldering fires described by Zhang, Boggs and Murray, "Effect of Limiting Airflow in Mitigating Combustion-Driven Manhole Events," *IEEE Electrical Insulation Magazine*, Vol. 27, No. 6, 2011) occur with some frequency on aged power networks. See, for example, FIG. 8A of U.S. patent application Ser. No. 16/190, 832, which illustrates 18 fire events recorded over a 63 day period from May 10, 2018 to Jul. 12, 2018 in a New England city.

Vault owners desire to limit the damage caused by fires within connections of an underground manhole system. Further, vault owners wish to replace faulty cable(s) that cause such fires before power is lost, a larger fire erupts, carbon monoxide or other noxious gases leak into private premises (such as private premises PP illustrated in FIG. 1), or conditions for an explosion at a vault or private premises are triggered.

Duct Plugs

So called "duct plugs" have been in use for many decades. The term "plug" is an unfortunate word choice, because the term implies that a "duct plug" provides a gas-tight seal. Indeed, some marketers of these products claim that duct plugs can seal flammable gases in the connections (e.g., connections 104 illustrated in FIG. 1) and thus keep dangerous gases out of the vaults (e.g., vaults 102 illustrated in FIG. 1) where they can lead to explosions. Common types of duct plugs include expanding foam, expanding resin, modular, inflatable bags, and engineered duct sealing mastics.

Maintaining a multi-year, gas-tight seal (to one or two atmospheres of pressure) in the adverse conditions typically present in underground vaults is no easy accomplishment. Particularly challenging is the substantial temperature cycling that occurs on power cables. Cables cycle diurnally (discussed below) and necessarily expand and contract both radially and axially. Referring to FIG. 1, despite the imperfectness of creating a long-term gas-tight seal, attempting to do so makes sense where the utility vault C-3 is connected to the private premises PP by a connection C3-PP to prevent subjecting any occupants of the private premises PP to any flammable and/or poisonous gases present in the vault C-3. Carbon monoxide is a particular problem. In normal practice, but not illustrated in FIG. 1, each of the vaults 102 may include multiple such connections to different private premises.

While a single robust seal in the connection C3-PP at the private premises PP is required by the National Fire Protection Code ("NFPC"), creating a second seal in the connection C3-PP at the opposite terminus (at the vault C-3) is problematic because currently available duct plugs fail within the harsh environment present in the vault C-3.

Referring to FIG. 2, each of the connections 104 (see FIG. 1), defines an internal annulus 208. For simplicity, the irregular cross sectional area within each of the connections 104 (see FIG. 1), excluding the cross-sectional area of the cables Phase A, Phase B, Phase C, and Neutral, is referred to herein as an annular area and its extension to the axial length as an annular volume. This reference includes the traditional definition of annular together with interstitial spaces defined between and among the cables.

Tracking

FIG. 3 is an illustration of cables 300 exhibiting a phenomenon referred to as "tracking," which is all too prevalent in secondary electrical networks. As secondary cables age, they develop cracks 302 and 304 in their insulation layers allowing electricity 310 to flow over the outside surface of these cables between the cracks 302 and 304. This electricity 310 may flow between neighboring conductors, which means electricity may flow between cables having different phases (e.g., the cables Phase A, Phase B, and Phase C illustrated in FIG. 2), the system neutral (e.g., the cable Neutral illustrated in FIG. 2), and any proximate ground (e.g., water, earth, communication cables, water pipes, and the like). The electrical current flow follows a relatively high impedance path and energy is dissipated as heat in proportion to the relationship $I^2R$, where the variable "I" represents the root mean square (RMS) alternating current and the variable "R" represents resistance. As one of ordinary skill in the art would recognize, DC current would behave in a similar fashion.

This current leakage caused by tracking can persist for months or years, because current overvoltage protection in such networks is inherently tolerant of modest current losses. Put another way, cables and their protective systems are designed to carry several hundred amperes and are unperturbed by several amps of leakage current. The resulting localized heat can pyrolyze insulation polymer and ignite combustion of the cable surface as described in detail by Zhang et al. (Ibid). The cable surface materials are complex filled hetero-polymers. These polymers are generally plastic or elastomeric with fillers including clays, other inorganic fillers, and/or carbon black. Current flowing on the surface may ionize the air to plasma on a microscopic scale. Such micro-plasma events create local heating in excess of 16,900K. While fire is discussed in the next section, leakage currents are discussed in an Electron Balance section below.

Black Smokers

Zhang et al. (Ibid) describes restricting airflow in ducts to prevent extensive fires within those ducts. Such extensive fires produce copious black smoke and are referred to as "black smokers." Zhang et al. (Ibid) erroneously concludes the following:

We can compute that when airflow is controlled so that the molar flow ratio of nitrogen plus other minor inflow species to CO becomes greater than 7.3, the CO concentration cannot reach its lower explosive limit as a result of the diluting effect of the nitrogen and the other gas species. Thus smolder propagation in the duct causes only smoking manholes rather than a manhole fire or explosion. In other words, combustion-driven manhole events can be limited to relatively minor smokers by controlling the airflow rate.

It is of course desirable to prevent or limit the size of black smokers, but explosion risk cannot be ruled out by duct flow restrictions alone. If a connection employs duct seals (e.g., duct plugs) at one of both of its termini and one or more cables therein experiences tracking, two unfortunate things may happen. First, with a dearth of oxygen available (precluded or greatly restricted by the duct seals), very little combustion will occur and instead the chemical reactions near the tracking will be dominated by pyrolysis and plasmatization. In other words, with little oxygen present, the primary by-products of the reactions are hydrogen ($H_2$), hydrocarbons ($C_nH_m$, where n is 1 to about 6, and m is between 2n and 2n+2), atomic carbon (C), a small amount of carbon monoxide (CO), and even smaller amounts of carbon dioxide ($CO_2$) and water ($H_2O$). All of these by-products, except carbon dioxide ($CO_2$) and water ($H_2O$), are flammable and potentially explosive.

Second, if the connection includes two duct seals, driven by the energy supplied by the surface tracking, the pressure in the "sealed" portion of the connection will rise until at least one of the seals fails. When the seal fails, the flammable gases spew into the connected vault, or even worse, the connected private premises. These gases may ignite and explode, contribute to a fire, or poison people and/or other living things. Referring to FIG. 1, a single duct plug (not shown) installed in the terminus of the connection C3-PP at the private premises PP safely prevents contamination of the private premises PP, because gases exiting from the connection C3-PP will predominantly follow the easy, unconstrained path into the vault C-3. Zhang et al. (Ibid) failed to examine annular gas velocities below 0.1 m/s and hence the conclusions (above) are partially erroneous. As annular gas velocity approaches zero, the supply of oxygen also approaches zero, hydrogen and hydrocarbons are produced in greater quantities, and CO production declines. Thus, the reassurance provided by Zhang et al. is ill-founded.

Black Smokers Versus Explosions

Without duct plugs installed, fresh air and oxygen required to fuel an exothermic chemical reaction (such as oxidative decomposition), which is a self-sustaining conflagration, is limited in size indirectly by the pressure differential between the duct termini and the geometry (cross-section and length) of the annular flow path. Referring to FIG. 2, those parameters establish the maximum air flow rate through the annulus 208, which determines the maximum burn rate. Since pyrolysis is endothermic, it will not proceed beyond the energy input supplied by tracking (or leakage current) without the exothermic contribution of oxidative decomposition.

When a fire first kindles, there is approximately an atmospheric quantity of oxygen (about 21%) in the adjacent annular volume. As the oxygen is consumed and gaseous by-products are produced, those by-products must flow along a generally horizontal path until they spill into an adjacent vault. Of course, if the connection is sloped, this flow is likely to proceed predominately up-slope due to the low density of hot gaseous by-products. This tendency can be overridden by differential pressures at the duct termini by any number of mechanisms. For example, a northwesterly wind blowing aggressively down Broadway can induce a negative pressure because of the Bernoulli Effect on a vented manhole cover located on Broadway. If the vault on Broadway is connected to a second vault on east-west oriented Madison Avenue, air flow will be urged from the Madison Avenue vault toward the Broadway vault. If the induced pressure differential is greater than the buoyancy of the hot gaseous by-products, the flow may be downhill.

In any case, the gaseous by-products must ultimately flow from the source (fire) somewhere along the length of the connection toward one of its termini. If unidirectional flow is not established, the fire will remain small and be dominated by pyrolysis. This is the most benign smoldering fire case, but is particularly dangerous in connected unvented or passively vented vaults because the flammable pyrolysis products can accumulate in these unventilated or under-ventilated structures. If substantial unidirectional flow is established, it may become self-sustaining, if the rate of hot gases spilling into a vault is sufficient to create a chimney effect when those gases rise into the vault's chimney and vent to the surface. This chimney effect creates a negative pressure in the vault and draws more air into those connections connected to the vault, including the connection with the fire (e.g., the connection BB12 illustrated in FIG. 1).

Diurnal Breathing

Even in the absence of a pressure differential between two adjacent vaults connected by connections (e.g., ducts), air flows in the connections due to diurnal variation in network cable loading. Each cable has its own diurnal variation depending upon the customer loads served, the weather, and countless other factors. Network cables typically have design maximum conductor temperature ratings from 90° C. to 130° C.

When loads are very low, the cable temperature can drop to near the soil temperature at the depth where the connections are buried, which is typically about 2 to 5 meters. The soil temperature is not the ambient earth soil temperature as a great deal of waste heat is dissipated into the earth, which stores that energy. None-the-less, the temperature of the cable may drop to 20° C. to 30° C. depending on the season and location. In short, it is not unusual to have diurnal temperature variations is high as 100° C., more typically 50° C., but generally more than 20° C. From the ideal gas law, the change in volume caused by such diurnal temperature swings is approximately 33%, 17%, and 7% respectively. Thus, as load increases on cables, the temperature increases from impedance losses and these temperature increases are quickly conveyed by conduction, convection, and radiation (radiation to duct wall and then conduction to gases) to the surrounding gases, which forces 7% to 33% of the air from the annulus 208 (see FIG. 2). Conversely, as the cable and the gases in the connection cool, fresh air is drawn from connected vaults in the same proportion.

Dangerous Environment

Referring to FIG. 1, individuals who work in vaults operate in very dangerous environments. The risk of electrical shock, flash burns, suffocation, and poisoning (e.g., by CO and $H_2S$) are confronted daily. It has been common practice, and a U.S. OSHA requirement, that before and during worker entry into the confined space of a vault (e.g., the vault B-1) that a blower (e.g., a blower 120) is used to supply fresh air into a hose (e.g., a hose 122) that extends into the confined environment of the vault. The hose 122 that conveys the fresh air is generally made of a polymer, such as nylon or PVC. Unfortunately, the devices deployed to this end are unsatisfactory if an arc flash or explosion occurs inside the vault B-1 while a worker 130 is present. For example, this has happened on more than a single occasion at Consolidated Edison ("ConEd") where high temperature and an explosion blast destroyed the hose supplying fresh air to workers.

In one event, which was documented in the New York Times (https://www.nytimes.com/2008/10/10nyregion/10manhole.html), a worker died at least in part because the hose (which was like the hose 122) melted and fresh, cool air could not otherwise be supplied. In an earlier event that occurred in the 1970's, a ConEd employee named Dan Simon survived by breathing fresh air that poured into the vault through the connections. During that event, a 60 to 120 second arc flash filled the vault to the top with super-hot air. The hose melted and failed within moments of the arc flash initiation. Fortunately, Mr. Simon was able to drop to the floor of the vault where he found enough cool air to breath until the limiters (i.e., fuse-like devices that melt and end current flow) finally operated.

Electron Balance

Under normal, non-leaking circumstances, the current flowing down the length of a cable is precisely the same along its entire length. That is, properly calibrated first and second ammeters positioned at first and second ends, respectively, of a first cable extending through a connection (e.g., a duct) will measure the same current at or near the connection termini. The consequence of current leakage (e.g., caused by tracking) is that the currents at the aforementioned connection termini will no longer be the same. The current loss from this first cable may bleed to one or more second cables in the same connection, the system neutral in the same connection, or to any proximate ground (e.g., water, the earth, communication cables, water pipes, and the like). If the current bleed is to one or more second phase conductors, the net current lost will approximately balance and similar measurements on at least one other conductor will be likewise perturbed. If the current leaks to the system neutral, a similar perturbation may be observed in the neutral current flow. Because neutrals are often bare conductors and leak to any available ground, an electron balance is likely to have less fidelity than interphase leakage.

BRIEF DESCRIPTION OF THE SEVERAL VIEWS OF THE DRAWING(S)

Like reference numerals have been used in the figures to identify like components.

DETAILED DESCRIPTION OF THE INVENTION

The term "fire" used below refers to any gas generating event, including plasmatization, pyrolysis, and/or oxidative decomposition.

Duct Flow Restrictor

Figure 4A:
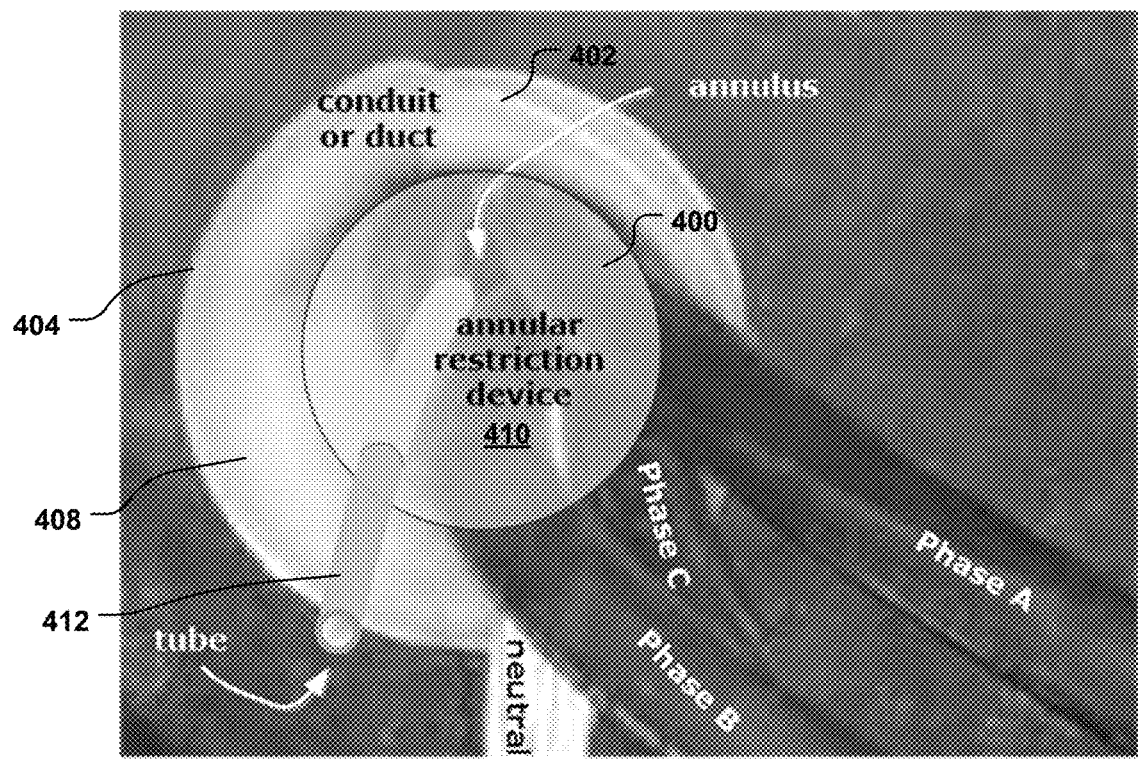
FIG. 4A is an end view of a first duct flow restrictor installed in a connection.
Figure 4B:
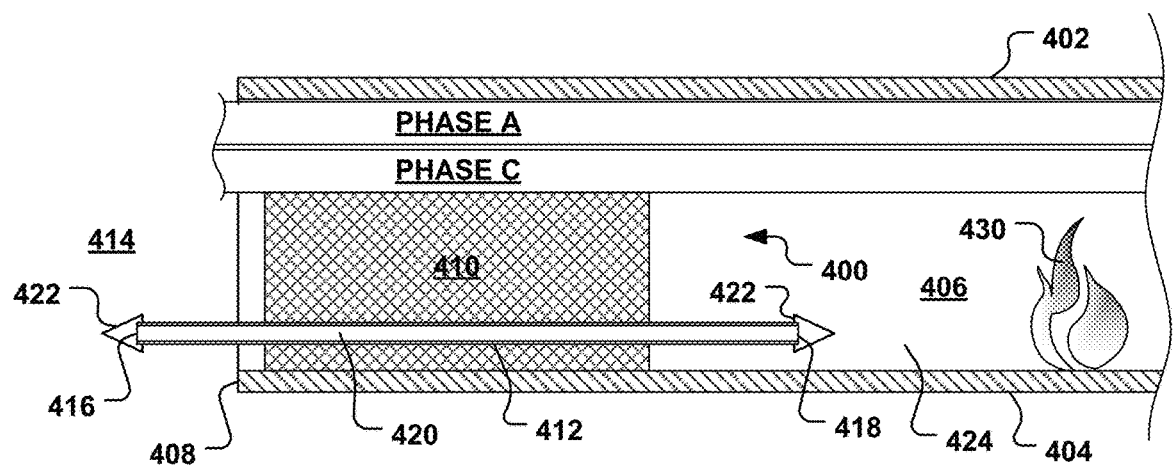
FIG. 4B is a side cross-sectional view of the first duct flow restrictor installed in the connection.

FIGS. 4A and 4B illustrate a duct flow restrictor 400 installed in a connection 402 (e.g., a duct). The inventors have discovered that sealing connections (like the connection 402) is counter-productive and that allowing large quantities of air to flow though connections is also not advisable. The former causes explosions and the latter causes large fires.

The duct flow restrictor 400 includes an annular restriction device 410 and a concentration member 412. The duct flow restrictor 400 is configured to restrict the flow of air through the connection 402. The restricted flow may help prevent large fires. The restricted flow may help with identifying which of the connections harbors a fire by urging the bulk of a flow of flammable gas through the concentration member 412.

Referring to FIG. 4B, the connection 402 has a conduit wall 404 that defines annular space or annulus 406. In this example, cables Phase A, Phase B, Phase C, and Neutral (see FIG. 4A) travel axially through the annulus 406. The annular restriction device 410 may be installed near a first terminus 408 (e.g., in a vault 414) of the connection 402. The annular restriction device 410 fills substantially all of a portion of the annulus 406 located between the cables Phase A, Phase B, Phase C, and Neutral and the conduit wall 404, but need not form a fluid-tight seal with either the conduit wall 404 or the cables Phase A, Phase B, Phase C, and Neutral.

The concentration member 412 may be implemented as a tube. In such embodiments, the concentration member 412 has a nominal outer diameter ("OD") and a nominal inner diameter ("ID"). By way of a non-limiting example, the nominal OD may be about ⅜ inches and the nominal ID may be about ¼ inches. By way of non-limiting examples, the concentration member 412 may be constructed from one or more polymeric and/or metallic materials.

The concentration member 412 extends through the annular restriction device 410 and allows both fresh and contaminated air to flow therethrough. A first end 416 of the concentration member 412 extends outwardly beyond the annular restriction device 410 and is positioned inside the vault 414. A second end 418 of the concentration member 412 extends into the connection 402 beyond the annular restriction device 410 and is positioned inside the annulus 406 behind the annular restriction device 410. An open-ended through-channel 420 extends between the first and second ends 416 and 418.

To avoid fouling the concentration member 412, at least one of the first and second ends 416 and 418 may incorporate an antifouling feature 422 configured to prevent debris (e.g., insects, arachnids, or flotsam) from entering and/or plugging the through-channel 420 of the concentration member 412. FIG. 4B illustrates separate antifouling features 422 positioned on each of the first and second ends 416 and 418. The antifouling feature(s) 422 may each be implemented as a screen or other well-known mechanism configured to prevent insects, arachnids, and/or flotsam from entering and/or plugging the through-channel 420 of the concentration member 412. In FIG. 4B, the antifouling features 422 have each been implemented as a conically shaped screen having an apex that is spaced apart from the concentration member 412.

The concentration member 412 may extend through the annular restriction device 410 within a bottom portion 424 of the connection 402. Thus, the concentration member 412 may be positioned near the bottom of the connection 402 to facilitate the drainage of water (ubiquitous in duct-manhole environments) and/or other liquids from the annulus 406 of the connection 402. The concentration member 412 may be substantially straight to prevent any water accumulation in the through-channel 420 of the concentration member 412. The concentration member 412 may be generally horizontal to allow liquid to freely drain from both the connection 402 and the concentration member 412. More than 50% of volumetric flow through the connection 402 may pass though the concentration member 412 of the duct flow restrictor 400. For example, the annular restriction device 410 may restrict air velocity through the annulus 406 to less than 0.1 meter per sec (m/sec) or less than 0.5 m/sec.

Many "ducts plugs" are currently available in the market. By way of a non-limiting example, the duct flow restrictor 400 may be constructed by selecting a duct plug that fills substantially all of the annular space between the cables Phase A, Phase B, Phase C, and Neutral and the conduit wall 404, and modifying the duct plug to allow the concentration member 412 to pass therethrough.

The duct flow restrictor 400 limits the size of a fire 430 inside the connection 402 by restricting the flow of gas (e.g., oxygen) to the fire 430. The duct flow restrictor 400 may concentrate and amplify perturbations in the gases generated by the fire 430 making them easier to detect. For example, the annular restriction device 410 may concentrate the flow of gases by at least 2-fold or at least 10-fold. The concentration may occur within the concentration member 412.

Figure 1:
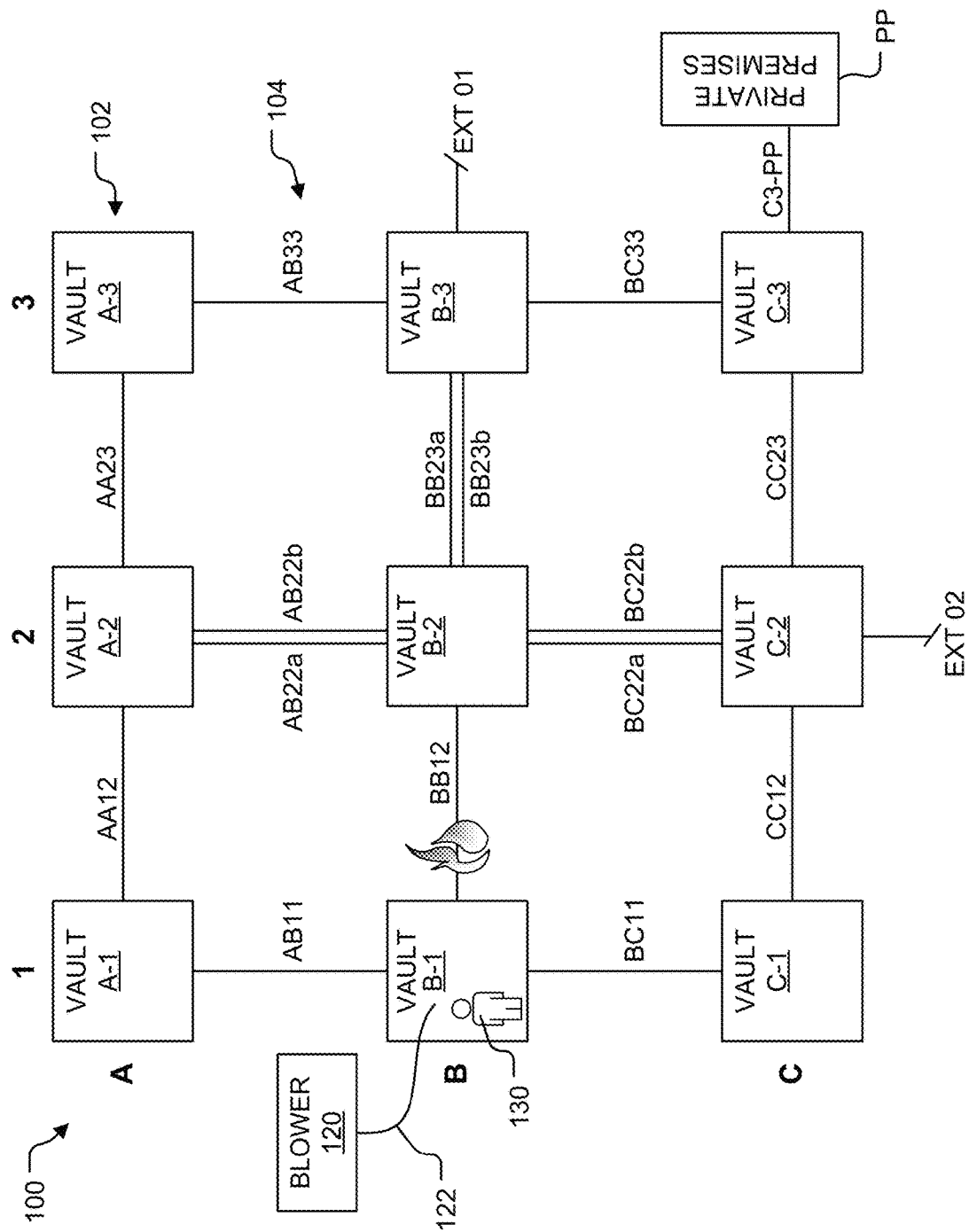
FIG. 1 is an illustration of a prior art network of underground vaults in which a fire is occurring in a connection interconnecting two of the vaults.
Figure 2:
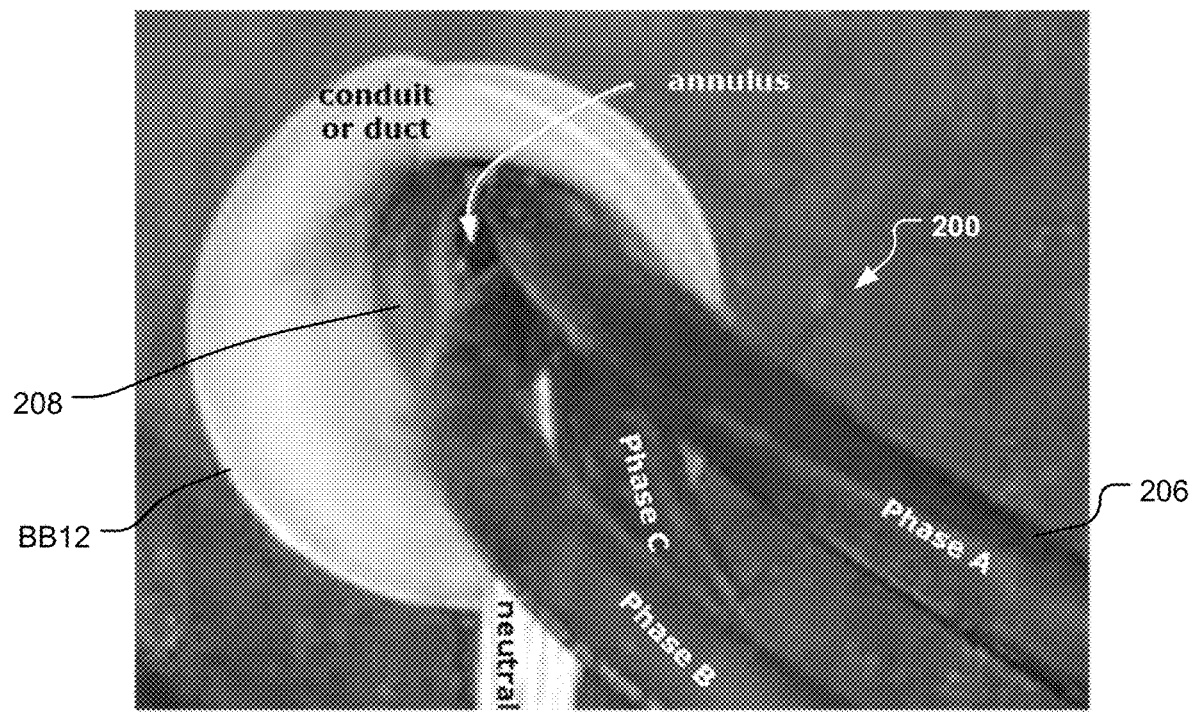
FIG. 2 illustrates a prior art connection housing an exemplary four-wire configuration of the type most often used in secondary electrical networks.
Figure 3:
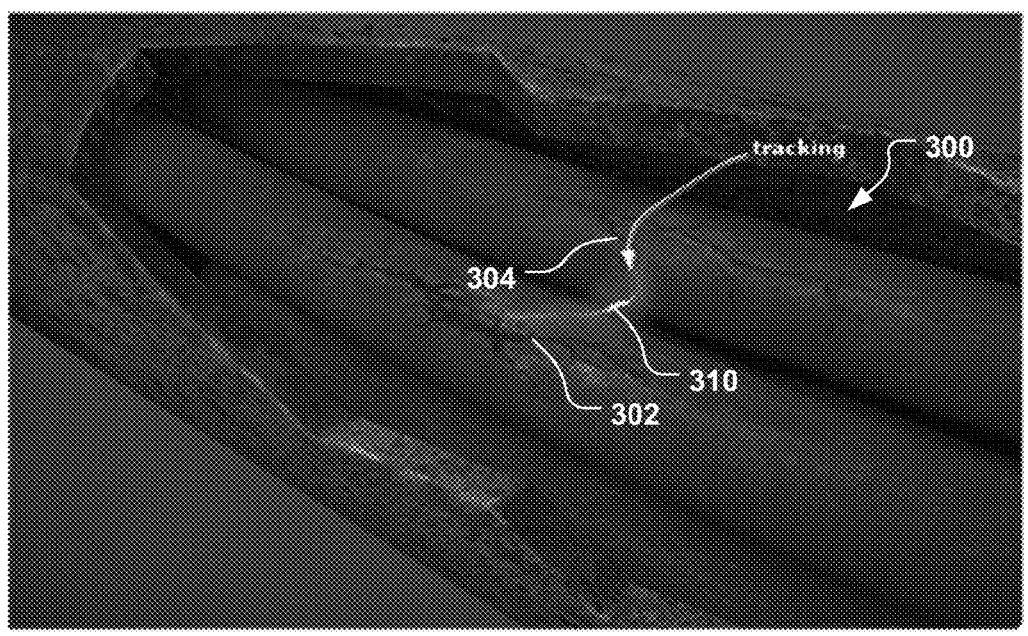
FIG. 3 is an illustration of prior art cables exhibiting tracking, which is commonly observed in secondary electrical networks.
Figure 5:
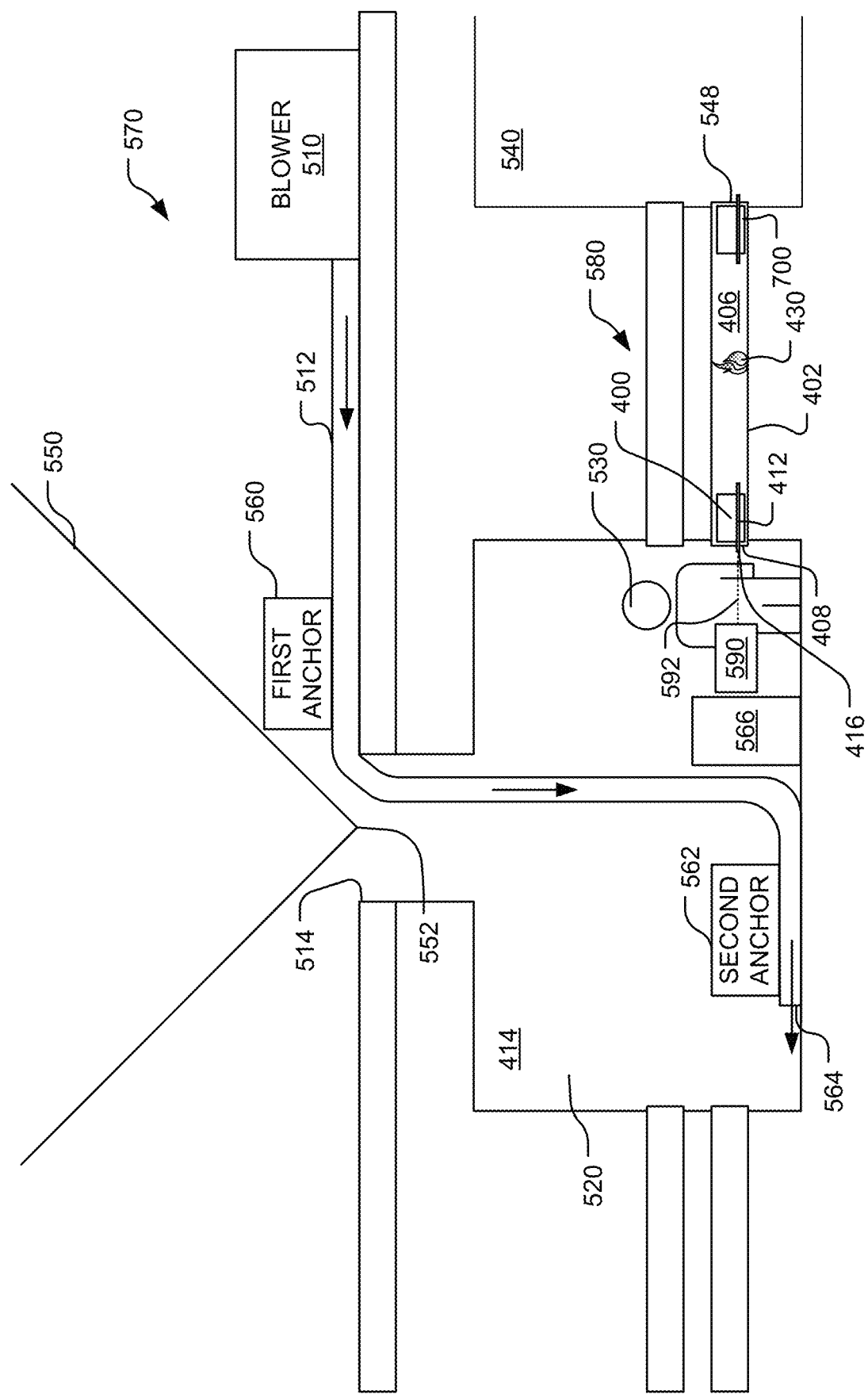
FIG. 5 is a cross-sectional view of a remote detector installed in an underground vault connected to the connection of FIGS. 4A and 4B and positioned to collect remote measurements.

Referring to FIG. 1, as mentioned in the Background section above, the vaults 102 are very dangerous environments. When the air inside the vault B-1 becomes unbreathable, an emergency fresh air supply is needed for any personnel (e.g., the worker 130) inside the vaults 102. Referring to FIG. 5, a blower 510 supplies fresh air into a receiving end 516 (see FIG. 8) of a hose 512 that extends through a manhole opening 514 and into a confined interior 520 of the vault 414 before and while a worker 530 is present in the vault 414. Thus, the receiving end 516 (see FIG. 8) is connectable to the blower 510 and configured to receive the fresh air from the blower 510. The vault 414 is interconnected with a vault 540 by the connection 402. The first terminus 408 of the connection 402 opens into the vault 414. A second terminus 548 opens into the vault 540. As explained in the Background section, prior art duct plugs significantly reduce air flow through the connections 104 (see FIG. 1). Completely removing or significantly reducing the flow of fresh air into the vault 414 poses a risk to human life. Thus, if, as occurred in the exemplary ConEd events described in the Background section above, the vault 414 fills with smoke, the worker 530 needs to be able to receive fresh air from an adjacent vault 540 through the connection 402. The duct flow restrictor 400 allows fresh air to pass through the concentration member 412 and into the vault 414 where the fresh air may be breathed by the worker 530 (e.g., in the event of a fire and/or an explosion).

Pinpointing a Fire within a Connection

Referring to FIG. 5, this section describes a convenient method of pinpointing in which connection, of a plurality of connections 580 that are typically entering and exiting the vault 414, the fire 430 is occurring. The number of connections 580 having a terminus in the vault 414 can be quite large. Some transmission and distribution vaults may have only two connections in which the phase cables Phase A, Phase B, and Phase C are housed together in a single connection. Alternatively, a vault may have six ducts if each of the phase cables Phase A, Phase B, and Phase C is housed in a separate connection. If a circuit branches within a vault or more than one circuit utilizes the same vault, the number of connection termini increases. In secondary electrical networks, the number of connections with a terminus in a single vault is generally much higher. Dozens of connection termini are the norm. Whether the number of connection termini is two or 144, vault owners must identify the specific connection that is harboring the fire 430 to effectuate repairs because it is not practical to begin removing cables at random. Some clear evidence pointing to the offending connection is needed.

As mentioned above, the duct flow restrictor 400 may concentrate and/or amplify perturbations in the gases generated by the fire 430 making them easier to detect. This concentration and/or amplification facilitates detecting or measuring fire-caused perturbations of the gases in the annulus 406 and allows specific connection(s) harboring fire(s) to be positively identified. Perturbations from the fire 430 include, but are not limited to, changes to the following:
1. Temperature;
2. concentrations of gases (e.g., by-products from combustion, by-products from pyrolysis, by-products from plasmatization, oxygen, and/or nitrogen, referred to hereinafter collectively as "Analytes");
3. particulates (e.g., soot, ash, etc.);
4. gaseous carbon;
5. steam;
6. gas flow direction;
7. gas flow rate;
8. sound; and
9. light.

Figure 6:
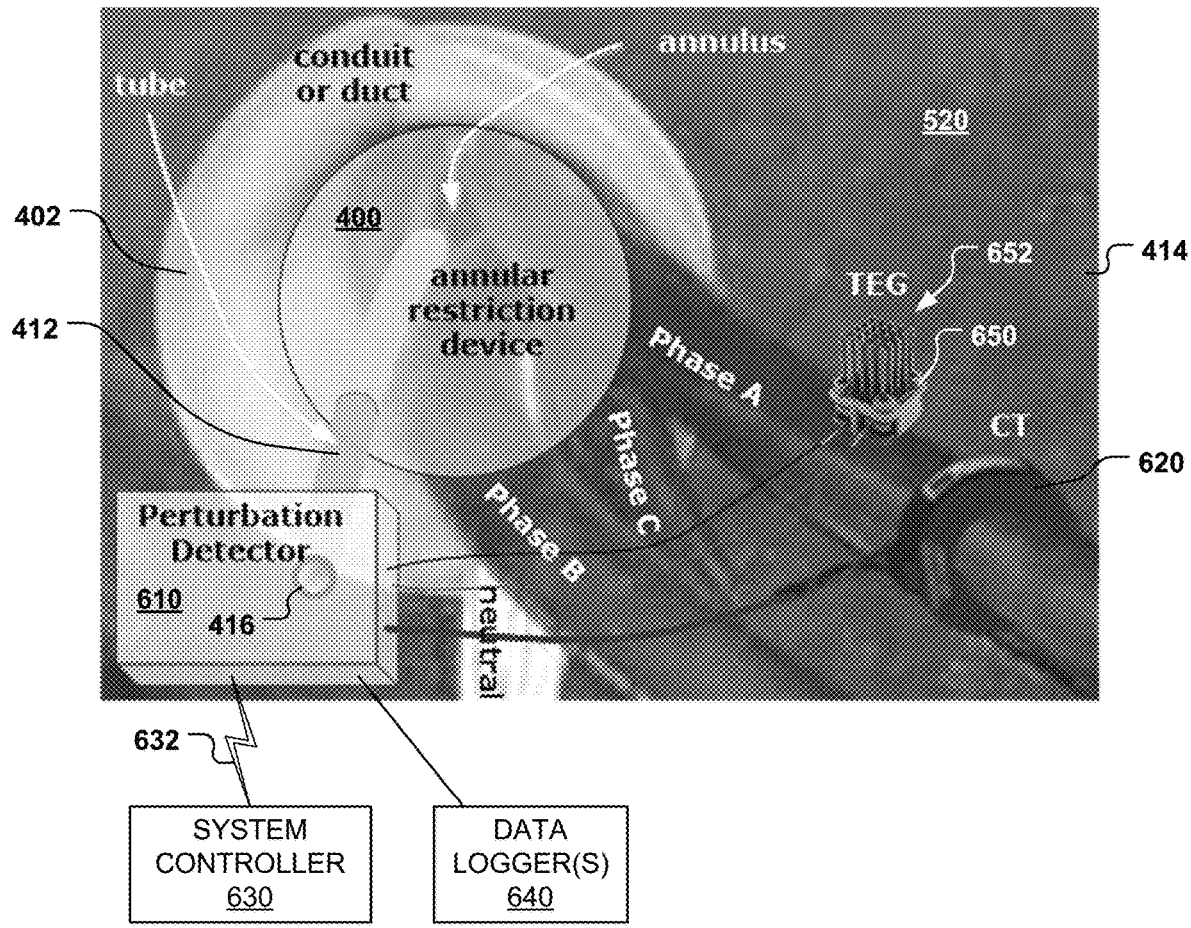
FIG. 6 is an end view of a first perturbation detector positioned to collect in-line measurements.

Referring to FIG. 6, at least one perturbation detector 610 is used to detect changes in one or more of the above. The perturbation detector 610 may be deployed within, at, or near the first end 416 of the concentration member 412 and used to obtain in-line measurements. The perturbation detector 610 may include a thermocouple, thermistor, mechanical temperature gauge, and/or IR sensor (local or remote) configured to obtain in-line temperature measurements. The perturbation detector 610 may include an electronic analyte device, a reagent configured to detect reversible or irreversible chemical reactions, an adsorbent, and/or an absorbent configured to obtain in-line analyte (e.g., gas) concentration measurements. The perturbation detector 610 may include electronic gas detection equipment, such as non-dispersive infrared ("NDIR") equipment and/or electrochemical equipment, configured to obtain in-line analyte (e.g., gas) concentration measurements. The perturbation detector 610 may include ion detectors, light scattering sensors, and visual sensors (UV, visible, and/or IR) configured to obtain in-line particulate measurements. In-line particulate measurements may be obtained by allowing particles to deposit on filtration media and detecting the deposited particulates visually or electronically (e.g., optical sensing of the deposition surface). The perturbation detector 610 may collect gaseous carbon (atomic carbon, nano-scale agglomerates of carbon, and/or micro-scale agglomerates of carbon) on one or more cool surfaces. The perturbation detector 610 may include a visible light camera (still or video), an IR camera (still or video), or a light scattering sensor configured to obtain in-line steam measurements. The perturbation detector 610 may include one or more devices configured to collect in-line measurements of the gas flow rate using the Coriolis Effect, differential pressure measurements, ultrasonic measurements, optical measurement, or thermal dispersion measurements. The perturbation detector 610 may include a microphone configured to obtain in-line sound measurements. The perturbation detector 610 may optionally include an amplifier and/or suitable frequency filters configured to attenuate sound outside of relevant frequencies. The perturbation detector 610 may include a photodetector configured to obtain in-line light (UV, visible, or IR) measurements.

Figure 7:
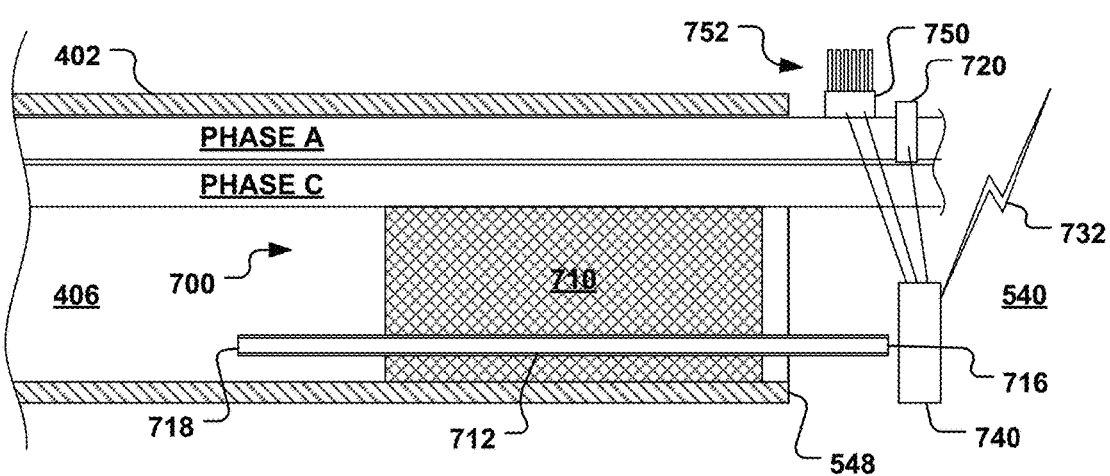
FIG. 7 is a side cross-sectional view of a second duct flow restrictor installed in the connection and a second perturbation detector positioned to collect in-line measurements.

FIG. 4B depicts the duct flow restrictor 400 installed in the connection 402 at or near the first terminus 408 and FIG. 7 depicts a duct flow restrictor 700 installed in the connection 402 at or near the second terminus 548. Referring to FIG. 7, the duct flow restrictor 700 is substantially identical to the duct flow restrictor 400 (see FIGS. 4A-6). Therefore, the duct flow restrictor 700 includes an annular restriction device 710 and a concentration member 712. For ease of illustration, the optional antifouling features 422 (see FIG. 4B) have been omitted from FIG. 7. However, one or both of first and second ends 716 and 718 of the concentration member 712 may include the antifouling feature 422 (see FIG. 4B). In this example, a perturbation detector 740 is deployed within, at, or near the first end 716 of the concentration member 712 and used to obtain in-line measurements. The perturbation detector 740 may be substantially identical to the perturbation detector 610 (see FIG. 6).

Alternatively, instead of collecting in-line measurements, the perturbation detector 610 (see FIG. 6) and/or the perturbation detector 740 may each be configured to collect remote measurements. For example, referring to FIG. 5, the perturbation detector 610 may be implemented as or include at least one remote detector 590 positioned so that it has a line-of-sight 592 with the first end 416 and/or the second end 418 (see FIG. 4B) of the concentration member 412. The remote detector(s) 590 may be implemented as one or more light scattering sensor, one or more visual sensor, and the like. By way of another non-limiting example, the remote detector(s) 590 may be configured to perform remote analyte sensing using one or more methods described in U.S. Pat. No. 8,013,303, titled "Mobile Remote Detection of Fluids by a Laser," issued to Ershov et al. However, the remote detector(s) 590 may not be mobile in the sense proposed by Ershov et al.

The remote detector(s) 590 may be implemented as at least one laser detector installed in a permanent location within the vault 414. The laser detector(s) may scan the interior 520 of the vault 414 by rotating about at least one axis. For example, the laser detector(s) may be configured to move or rotate about two axes. To obtain full visual coverage of the interior 520 of the vault 414, the laser detector(s) may be configured to transit along at least one axis.

Referring to FIG. 5, in this example, the perturbation detector 610 (see FIG. 6) has been implemented as the remote detector 590 (e.g., a laser detector). The first end 416 of the concentration member 412 is positioned within the line of sight 592 of the remote detector 590. In embodiments in which the remote detector 590 is implemented as a laser detector, an optional target (not shown) may be used to facilitate aiming the laser. The target (not shown) is configured to help the remote detector 590 (e.g., a camera) find the first end 416 of the concentration member 412 by reflecting the laser light back toward the remote detector 590 (e.g., an infrared sensor of the remote detector 590). The target (not shown) may be appropriately reflective to maximize the return signal of the laser light. By way of a non-limiting example, the laser may be implemented as an infrared laser.

Another approach that does not require using the duct flow restrictor 400 is to measure the current of at least one of the phase cables (e.g., one of the cables Phase A, Phase B, and Phase C) with a pair of current transformers ("CTs"). FIG. 6 illustrates a first CT 620 connected to the cable Phase A. FIG. 7 illustrates a second CT 720 connected to the cable Phase A near the second terminus 548 of the connection 402. Referring to FIG. 6, the CTs 620 and 720 (see FIG. 7) may be substantially identical to one another. The pair of CTs 620 and 720 (see FIG. 7) may be used to detect a current imbalance on the cable Phase A, which is evidence of a faulty cable that should be rehabilitated. In some embodiments, each of the cables Phase A, Phase B, and Phase C and the cable Neutral may be connected to its own pair of CTs (like the CTs 620 and 720) to allow a complete electron balance over the length of the connection 402.

Some of the above approaches to detecting perturbations involve electronic devices while some are mechanical. For example, the perturbation detector 610 and/or the CTs (e.g., the CT 620) at the first terminus 408, may each generate electronic signals encoding values of one or more properties measured by the perturbation detector 610 and/or the CTs. The electronic signals can be communicated to a system controller 630 over a communication link 632. The communication link 632 may be wired (e.g., including one or more wires) and/or wireless (e.g., using radio or infrared signals). Wired communications are feasible for transmission and distribution vaults housing only a handful of cables. Wireless signals may be used in crowded vault environments. By way of a non-limiting example, the perturbation detector 610 may communicate with the system controller 630 via a short range radio frequency signal (e.g., Bluetooth or Zigbee (IEEE 802.15.4)).

Similarly, referring to FIG. 7, the perturbation detector 740 and/or the CTs (e.g., the CT 720) at the second terminus 548, may each generate electronic signals encoding values of one or more properties measured by the perturbation detector 740 and/or the CTs. The electronic signals can be communicated to the system controller 630 (see FIG. 6) over a communication link 732 that is substantially identical to the communication link 632 (see FIG. 6).

Alternatively, referring to FIG. 6, the perturbation detectors 610 and 740 (see FIG. 7) and/or the CTs (e.g., the CTs 620 and 720) may be connected to one or more data loggers 640 configured to store data. The data logger(s) 640 may store the data on a first-in, first-out basis (e.g., using a ring buffer). The data logger(s) 640 may be read by personnel (e.g., the worker 530 illustrated in FIG. 5) after an event is detected or experienced by other means.

Mechanical devices may be read remotely with cameras or observed directly by a human operator (e.g., the worker 530 illustrated in FIG. 5). For example, referring to FIG. 6, the concentration member 412 may flow into a finned metallic heat sink (not shown) designed to encourage the deposition of carbon onto its surface. The heat sink may have a clam shell design so that the human operator may open it easily and inspect the inner surface for carbon deposits. Such deposits are indicative of a fire that includes plasmatization and/or pyrolysis.

Some of the approaches described above require electricity to operate. This electricity may be supplied by batteries or wires. By way of another non-limiting example, the electronic devices may receive power transmitted to the devices wirelessly or harvest power from the cables in the vault 414. Power may be transmitted wirelessly to these devices using photovoltaic (UV, visible, and/or IR) and RF signals. Power may be harvested wirelessly from the cables in the vault using the CTs (e.g., the CTs 620 and 720) and/or thermal electric generators ("TEGs"). The CTs provide reliable power and have the added benefit of being able to gather data on the current flowing though the cable to which the CT is attached. Power utilities often do not have a method to determine current flow on individual cables. In fact, in at least some circumstances, unusual current flows measured at a single point, particularly very high current and noisy (e.g., rapidly changing) current, may be related to the pinpointing of fire events. TEGs are reliable and use entirely wasted energy. As illustrated in FIG. 6, TEGs may be coupled with one or more of the CTs in combination to both harvest power and measure current flow.

Referring to FIG. 6, a first TEG 650 and the first CT 620 may both be attached to the cable Phase A. Similarly, FIG. 7 illustrates a second TEG 750 and the second CT 720 both attached to the cable Phase A. Referring to FIG. 6, the TEGs 650 and 750 (see FIG. 7) are each configured to harvest power from the waste heat of the cable Phase A. The cable Phase A is warmer than the surrounding air, which cools vertical rods 652 of the TEG 650 and cools vertical rods 752 (see FIG. 7) of the TEG 750 (see FIG. 7). This temperature difference allows each of the TEGs 650 and 750 (see FIG. 7) to generate DC electricity. The TEGs 650 and 750 (see FIG. 7) supply their respective electricity to the perturbation detectors 610 and 740, respectively. Additionally, the perturbation detectors 610 and 740 (see FIG. 7) may receive at least some of harvested electricity from the CTs 620 and 720 (see FIG. 7), respectively.

As explained above, the CTs 620 and 720 (see FIG. 7) may each measure the current in the cable Phase A. The current measured by the CT 620 may be communicated (e.g., via a wired connection) to the perturbation detector 610, which communicates the current measured to the system controller 630. Similarly, referring to FIG. 7, the current measured by the CT 720 may be communicated (e.g., via a wired connection) to the perturbation detector 740, which communicates the current measured to the system controller 630 (see FIG. 6). Referring to FIG. 6, the system controller 630 calculates a first current difference between the currents measured by the CTs 620 and 720 (see FIG. 7). Additionally, the system controller 630 may receive currents measured by the CTs attached to the cable Phase B at or near the termini 408 and 548 and calculate a second current difference between those currents. The system controller 630 may receive currents measured by the CTs attached to the cable Phase C at or near the termini 408 and 548 and calculate a third current difference between those currents. Also, the system controller 630 may receive currents measured by the CTs attached to the cable Neutral at or near the termini 408 and 548 and calculate a fourth current difference between those currents.

The system controller 630 determines the cable Phase A is not leaking current (e.g., via tracking) within the connection 402 when the currents measured by the CTs 620 and 720 (see FIG. 7) are approximately equal. In other words, the system controller 630 determines the cable Phase A is not leaking current when the first current difference is zero. On the other hand, the system controller 630 determines the cable Phase A is leaking current within the connection 402, when the currents measured by the CTs 620 and 720 (see FIG. 7) are different. In other words, the system controller 630 determines the cable Phase A is leaking current when the first current difference for the cable Phase A is non-zero. As explained above, the currents of the cables at the first terminus 408 should balance with the currents of the cables at the second terminus 548. Thus, if the cable Phase A is leaking current with one or more of the cables Phase B and Phase C, the first current difference will be approximately equal to the second current difference or the third current difference calculated for the cables Phase B and Phase C, respectively. Similarly, if the cable Phase A is leaking current to the cable Neutral, the first current difference may be approximately equal to the fourth current difference of the cable Neutral. However, if the cable Neutral is implemented as a bare conductor, the cable Neutral may leak to any available ground. Therefore, the electron balance is likely to have less fidelity than when it is used to determine inter-phase leakage.

As described above, the system controller 630 determines whether any of the cables Phase A, Phase B, and Phase C are leaking current. If the system controller 630 determines any of the cables Phase A, Phase B, and Phase C are leaking current, the system controller 630 notifies a user (e.g., the vault owner) as to which of the cable Phase A, Phase B, and Phase C are leaking. Thus, the system controller 630 may use the CTs to pinpoint sources of current leakage.

The perturbation detector 610 and/or the perturbation detector 740 (see FIG. 7) may each be used to determine values of one or more connection property and communicate those values to the system controller 630. In this example, the perturbation detector 610 is configured to measure the temperature of the gas flowing through the concentration member 412. For example, the perturbation detector 610 may include a thermistor, a thermocouple, or the like as well as any electrical components (e.g., circuits) required. The system controller 630 knows the temperature of the air in the vault 414 and/or another temperature measuring device (not shown) installed near the outer surface of the perturbation detector 610 may be used to directly measure the air temperature of the vault 414.

When the temperature within the concentration member 412 is close to the temperature of the air in the vault 414, the air is flowing into the concentration member 412 toward the connection 402, hereinafter "ductward." On the other hand, when the temperature within the concentration member 412 is approximately equal to or greater than the temperature of the cables Phase A, Phase B, and Phase C, the flow direction is outward from the connection 402 into the vault 414, hereinafter "vaultward."

The system controller 630 may estimate the temperature of each of the cables Phase A, Phase B, Phase C, and Neutral using direct and/or indirect measurements. The system controller 630 may obtain direct cable temperature measurements from a thermistor or IR sensor. The system controller 630 may obtain indirect cable temperature measurements by performing ampacity calculations on the current measurements obtained for each of the cables Phase A, Phase B, Phase C, and Neutral.

When the temperature within the concentration member 412 is greater than the estimated temperature of the cables Phase A, Phase B, Phase C, and Neutral by at least a threshold amount an exothermic event is likely occurring (e.g., electrical current leakage such as tracking or oxidative decomposition). The system controller 630 may determine the threshold amount using data collected during periods in which no events are suspected to have occurred. For example, the system controller 630 may compile the temperature within the concentration member 412 together with the estimated temperatures of the cables Phase A, Phase B, Phase C, and Neutral and calculate a standard error of a correlation between the temperatures. The system controller 630 may select the threshold amount such that normal data acquisition noise is ignored (e.g., variances within the standard error). Additional alarm conditions can be set at any number of thresholds, and the system controller 630 may calculate a probability of an exothermic event and communicate the probability to the user (e.g., vault owner).

If the sister perturbation detector 740 (see FIG. 7) is installed at or near the second terminus 548 of the connection 402, measurements from the perturbation detectors 610 and 740 (see FIG. 7) can be collected by the system controller 630 and used to deduce whether a gas-creating-event (e.g., the fire 430 illustrated in FIG. 4B) is occurring within the annulus 406 of the connection 402. When a gas-creating-event is occurring within the connection 402, gases will be flowing vaultward through both of the concentration members 412 and 712 (see FIG. 7) independently of whether there is a temperature perturbation. On the other hand, if gases are not flowing vaultward through both of the concentration members 412 and 712 (see FIG. 7), the gas-creating-event is not occurring within the connection 402 or is so small as to be negligible. Diurnal breathing confounds the flow of the gases because gases generally flow vaultward during the warming portion of the diurnal cycle and generally ductward during the cooling portion of the cycle. The system controller 630 may use a model of the diurnal cycles to compensate for some blindness to minor burning events during cooling cycles when the flow is generally ductward and during warming cycles when the flow is generally vaultward. Nevertheless, the temperature of the ductward flow will only exceed the temperature of the cables Phase A, Phase B, Phase C, and Neutral when there is an exothermic event.

In embodiments in which the perturbation detector 610 is configured to detect current measurements of at least one phase (or all of the phases) and the neutral, and the sister perturbation detector 740 (see FIG. 7) is installed at or near the second terminus 548 of the connection 402, the current measurements detected by the perturbation detectors 610 and 740 (see FIG. 7) can be used by the system controller 630 to deduce whether electrical current leakage is occurring on one or more of the cables using the method described above with respect to current measurements obtained from the CTs. While not necessary, the system controller 630 may measure the surface temperature and current of each of the phase cables Phase A, Phase B, and Phase C at both the first and second termini 408 and 548 of the connection 402 for cross corroboration.

The system controller 630 may be configured to alert the user (e.g., the vault owner) of the precise connection(s) harboring fire(s). The perturbation detectors 610 and 740 (see FIG. 7) may each optionally include an electrical storage device (e.g., battery, capacitor, and the like) to assure periodic updates to the system controller 630 if energy harvesting is intermittently insufficient.

Above, a method of measuring the perturbation of a property at the first terminus 408 of the connection 402 indicative of an ongoing fire has been described. The perturbation may be used to determine where the fire is located. The property may be one or more of a gas property, current, temperature, a flow vector, a concentration of an analyte, and concentration of a particulate. The system controller 630 may use measurements of multiple properties (e.g., a gas property and current) together for cross validation and/or to improve fidelity. The flow vector may include a direction and/or a flow rate. The analyte concentration may be measured in-line and/or remotely. The concentration of the particulate may be measured in-line and/or remotely. The concentration of the particulate may be determined by deposition and/or filtration. The concentration of the particulate allows the determination of whether there has or has not been a fire event since the last inspection of the deposition and/or filtration surfaces.

Using the methods described above, cables that are the source of small fires may be pinpointed so that they can be rehabilitated. Further, because the annular restriction device 410 and the annular restriction device 710 (see FIG. 7) limit air flow through the connection 402, the amount of oxygen inside the annulus 406 is limited to an amount insufficient to sustain a large fire or black smoker inside the connection 402. Thus, large fires and black smokers are not possible. Additionally, because the concentration member 412 and/or the concentration member 712 (see FIG. 7) allow at least some fresh air and some connection air to flow into and out of the connection 402, sufficient pressure cannot form within the sealed portion of the connection 402 to cause one of the annular restriction devices 410 and 710 (see FIG. 7) to fail due to tracking. Thus, the flammable gases will not spew into the vault 414, ignite, explode, contribute to a fire, or poison people and/or other living things. Likewise, referring to FIG. 5, if the connection 402 is connected to a private premises instead and in place of the vault 540, the flammable gases will not spew into the private premises if the private premises includes a suitable duct plug (not shown) but does not include the duct flow restrictor 700. In such an implementation, the duct flow restrictor 400, installed at or near the first terminus 408, allows all or almost all of the gases created in the connection 402 to flow away from the private premises and into the vault 414. If the vault 414 employs active ventilation, the flammable gases will be exhausted from the vault 414. In other words, explosions caused by gases created in the connection 402 by pyrolysis and/or plasmatization are not possible where such active ventilation is deployed. Examples of suitable systems that may be used to implement active ventilation are provided in U.S. patent application Ser. No. 15/173,633, filed on Jun. 4, 2016, and titled "Systems for Circulating Air Inside a Manhole Vault," U.S. patent application Ser. No. 15/084,321, filed on Mar. 29, 2016, and titled "Ventilation System for Manhole Vault," and U.S. patent application Ser. No. 15/476,775, filed on Mar. 31, 2017, and titled "Smart System for Manhole Event Suppression System." Each of the aforementioned patent applications is incorporated herein by reference in its entirety.

The system controller 630 supplied with the loading (e.g., currents) of cables Phase A, Phase B, and Phase C in the connection 402 (e.g., a duct) and the temperature of the air exiting and/or entering the connection 402 may model the flow of air to and/or from the connection 402. For example, the system controller 630 may perform a mass and energy balance and use it to predict the temperature and flow of the annular volume. Empirical observations taken over time allow the system controller 630 to accurately estimate otherwise difficult to model parameters, such as the mass, heat capacity, thermal conductivity, and temperature profile of the earth surrounding the connection 402. Example methods of performing a component mass balance and an energy balance are provided in U.S. patent application Ser. No. 16/190,832, filed on Nov. 14, 2018, and titled "Methods of Using Component Mass Balance to Evaluate Manhole Events," which is incorporated herein by reference in its entirety.

Robust Air Supply

FIG. 5 illustrates the blower 510 (e.g., a conventional blower) positioned well away from the manhole opening 514 (e.g., not within a 90° blast cone 550 with an apex 552 of the blast cone 550 being at the manhole opening 514) and connected to the hose 512. The hose 512 is constructed from a material that retains its functionality during and after exposure to an arc flash. The hose 512 is anchored by a first hose anchor 560 (e.g., a sandbag, similar heavy object, or a tie-down) positioned near the manhole opening 514, but outside of the blast cone 550, such that the hose 512 will not be displaced by the force of a blast overpressure (e.g., up to 15 psi). The hose 512 is similarly anchored by a second hose anchor 562 (e.g., a sandbag, similar heavy object, or an anchored tie-down) positioned at its discharge end 564. The hose 512 may have a cylindrical shape, but other cross sectional shapes, such as a polygon or ellipse, may be used.

The magnitude of a worst case arc flash may be determined using methods well known in the art. By way of a non-limiting example, the magnitude of an arc flash utilized to test suitable hose materials may be at least 15 kA, at least 25 kA, or at least 40 kA.

Arc exposure includes an arc current level expressed in kiloamps ("kA") and a Breakopen Threshold Performance ("BTP"), which is a product of the arc current level (kA) and an arc duration expressed as a number of cycles that cause breakopen. Thus, the BTP may be expressed in kA*cycles. The cycles may have a frequency of 60 Hz. As discussed herein, arc exposure values are assessed with respect to an arc that is perpendicular to, directed at, and 6 inches away from a hose material used to construct the hose 512.

The hose material is configured to withstand the effects of the worst case arc flash and an arc blast when the hose 512 is hung (e.g., nominally vertical) and/or anchored near energized equipment 566. Specifically, the hose material (1) is resistant to breakopen, (2) has sufficient mechanical strength, and (3) has the ability to self-extinguish flames following an arc exposure. The term "breakopen" refers to the formation of one or more holes in the hose material that may allow thermal energy to pass through the hose material.

Suitable hose materials include materials that can be exposed to an arc flash and not develop holes or otherwise break for at least a first predetermined amount of time and that self-extinguish within a second predetermined amount of time following the cessation of the arc flash. Breaks include material fragmentation or separation from any support hardware (e.g., steel spiral providing a backbone for a hose assembly and any fasteners that connect the steel spiral to the hose material). The first predetermined amount of time may be about ⅙th of a second, which is equivalent to 10 cycles at 60 Hz. Alternatively, the first predetermined amount of time may be about 60 seconds, which is equivalent to 3600 cycles at 60 Hz. The second predetermined amount of time may be about 30 seconds or less.

For example, the hose 512 may be constructed from a hose material that is flame retardant and mechanically robust (e.g., tear resistant and/or 15 psi blast resistant). Suitable hose materials are routinely utilized for arc suppression blankets. Non-limiting examples of suitable arc suppression blankets include a 25 KA arc suppression blanket sold by National Safety Apparel (Stock number K25LB4F5F), a 25 kA ArcGuard blanket sold by PMMI International (Stock number K25LB4F5F), and a 40 kA arc suppression blanket sold by Salsbury (Stock number ARC48-40). Such arc suppression blankets are generally constructed from multi-layered fabrics that include at least one layer configured to prevent ballistic penetration. The layer(s) may be constructed from a blast resistant material configured to at least withstand effects of a worst case arc flash in the vault 414. Examples of blast resistant materials that may be used to construct such layer(s) and the hose 512 include the following materials: poly-paraphenylene terephthalamide ("para-aramid") fiber, ultra-high molecular weight polyethylene ("UHMWPE"), polycarbonate material, carbon fiber composites, steel, and titanium. LEXAN® material is an example of a suitable polycarbonate material that may be used alone or combined with other materials to construct the hose 512. KEVLAR® material is an example of a suitable para-aramid fiber material that may be used alone or combined with other materials to construct the hose 512.

The blast resistant materials discussed above are also arc-flash-resistant. Thus, the hose 512 may be arc-flash-resistant. For example, referring to FIG. 8, the hose 512 may include an inner layer 802 constructed from a material that is at least blast resistant and is preferably arc-flash-resistant.

The hose may be constructed from a fire resistant material that self-extinguishes within the second predetermined amount of time of the end of the electrical arc flash. For example, the hose 512 may include an arc-facing or outer layer made of one or more flame retardant materials, such as polybenzimidazole ("PBI"), para-aramid fibers, poly-meta-phenylene isophthalamide ("meta-aramid") fibers, flame retardant ("FR") cotton, coated nylon, carbon foam ("CFOAM"), polyhydroquinone-dimidazopyridine, melamine treated flame retardant fibers, leather, and modacrylic. Modacrylic includes manufactured fibers in which the fiber-forming substance is any long-chain synthetic polymer composed of less than 85% by weight, but at least 35% by weight acrylonitrile units. NOMEX® material is an example of a suitable meta-aramid fiber material that may be used alone or combined with other materials to construct the hose 512.

Figure 8:
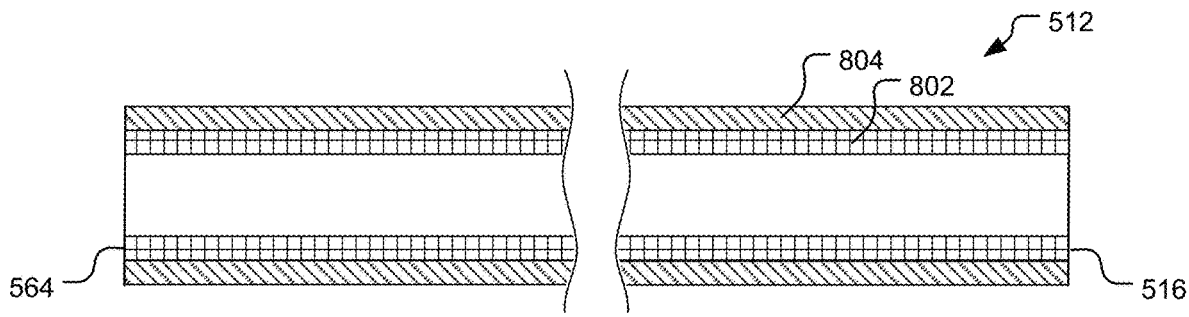
FIG. 8 is a longitudinal cross-sectional view of a hose configured to supply fresh air to an underground vault after an explosion has been initiated in the vault.

Referring to FIG. 8, the hose 512 may have an outer layer 804 constructed from one or more of the flame retardant materials discussed above. The hose 512 may be constructed from both the blast resistant material (e.g., the layer 802) and the fire resistant material (e.g., the layer 804). Thus, the hose may be blast-resistant, arc-flash-resistant, and fire-resistant. As one of ordinary skill in the art will recognize, the hose 512 may include at least a first layer (e.g., the outer layer 804 illustrated in FIG. 8), may include a second layer (e.g., the inner layer 802 illustrated in FIG. 8), or may include one or more additional layers (e.g., a third layer) as long as the final hose construction is blast-resistant, arc-flash-resistant, and fire-resistant. Further, the hose 512 may be rigid (e.g., metallic) or flexible (e.g., woven metals and/or polymeric fibers).

Referring to FIG. 5, as one of ordinary skill in the art will recognize, suitable hose material(s), whether composite or single layer, need not be gas tight, but must convey sufficient air to the discharge end 564 to supply fresh air to the bottom of the vault 414 to meet survival requirements of the worker 530 inside the vault 414. The minimum air flow rate is well known in the art and may be established by safety regulatory authorities, such as the Occupational Safety and Health Administration ("OSHA") in the United States.

The blower 510, hose 512, and anchors 560 and 562 may be characterized as forming a flash and explosion-proof fresh air supply system 570 configured to prevent air flow disruption by an explosion. The explosion may include an electrical arc flash and/or a chemical explosion. The system 570 is configured to provide sufficient breathable air to personnel (e.g., the worker 530) present in the vault 414 after an explosion. The hose 512 may be restrained (e.g., by the anchors 560 and 562), blast-resistant, arc-flash-resistant, and fire-resistant. The hose 512 is restrained by the first hose anchor 560 positioned at or near the manhole opening 514 and/or the second hose anchor 562 positioned at or near the discharge end 564 of the hose 512.

The arc-flash-resistant material may be any material configured to satisfy NFPA 70E-2015 and OSHA 29 CFR 1910.269. NFPA 70E-2015 is a standard of the National Fire Protection Association, and is the consensus 'Standard for Electrical Safety in the Workplace.' It was published in 1979. OSHA 29 CFR 1910.269 is an arc flash regulation for power generation, transmission, and distribution. In the United States, arc rated material must be rated as Flame Resistant per ASTM F1506. This includes a Vertical Flame Test to prove flame resistance, in addition to being tested per ASTM F1959 to determine the fabric's arc rating. In the United States, ASTM F2676-16, "Standard Test Method for Determining the Protective Performance of an Arc Protective Blanket for Electric Arc Hazards" defines the effectiveness of arc protective blankets in suppressing the combined effects of an arc flash and arc blast. The hose material may be configured to withstand the worst case arc-flash and satisfy ASTM F2676-16.

Figure 9:
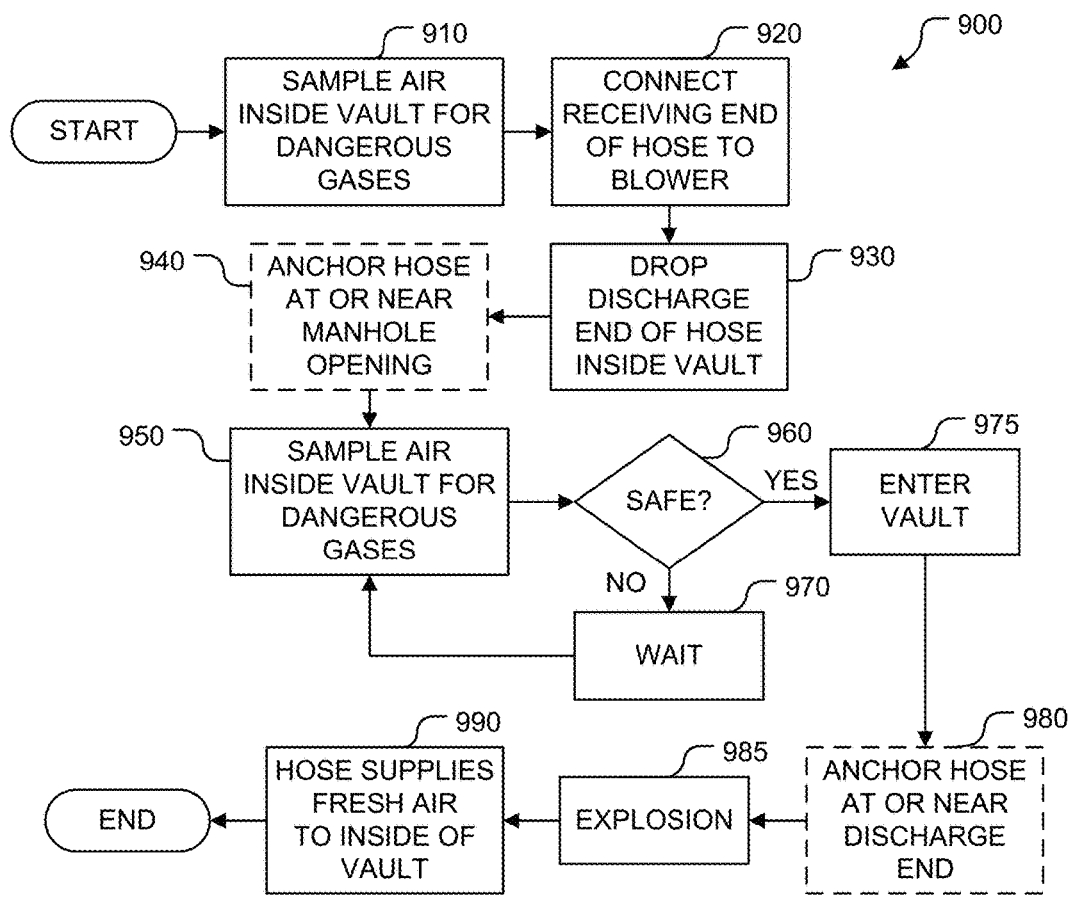
FIG. 9 is a flow diagram of a method of supplying fresh air to an underground vault after an explosion has occurred in the vault.

FIG. 9 is a flow diagram of a method 900 of providing an emergency fresh air supply to the vault 414 (see FIGS. 4B-6) after an explosion has occurred in the vault 414. At the start of the method 900, the worker 530 (see FIG. 5) intends to enter the vault 414 (see FIGS. 4B-6). In first block 910, the worker 530 (see FIG. 5) samples the air inside the vault 414 (see FIGS. 4B-6) for dangerous (poisonous and/or flammable) gases. Referring to FIG. 5, in next block 920 (see FIG. 9), the worker 530 connects the receiving end 516 (see FIG. 8) of the hose 512 to the blower 510, which is configured to supply fresh air to the receiving end 516 of the hose 512. In block 930 (see FIG. 9), the worker 530 drops the discharge end 564 of the hose 512 through the manhole opening 514 and into the interior 520 of the vault 414. The hose 512 conducts the fresh air to the discharge end 564, which discharges the fresh air into the vault 414. Optionally, the worker 530 may drop the second hose anchor 562 along with the discharge end 564. In optional block 940 (see FIG. 9), the worker 530 anchors the hose 512 (e.g., with the first hose anchor 560) at or near the manhole opening 514 to hold the hose 512 in place with respect to the vault 414.

In block 950 (see FIG. 9), the worker 530 (see FIG. 5) samples the air inside the vault 414 (see FIGS. 4B-6) for the dangerous gases. In decision block 960 (see FIG. 9), the worker 530 decides whether the blower 510 has blown enough fresh air into the vault 414 to reduce the dangerous gases to a safe level. When the worker 530 decides it is not safe to enter the vault 414, in block 970, the worker 530 waits and then returns to block 950 to resample the air inside the vault 414. On the other hand, when the worker 530 decides it is safe to enter the vault 414, in block 975, the worker 530 enters the vault 414. In optional block 980 (see FIG. 9), the worker 530 anchors the hose 512 (e.g., with the second hose anchor 562) at or near the discharge end 564 of the hose 512. For example, the worker 530 may connect the second hose anchor 562 to the discharge end 564 as soon as the worker 530 descends into the vault 414 to limit the worker's exposure to risk before the hose 512 is secured. Alternatively, if the second hose anchor 562 was dropped with the discharge end 564 (in block 930), in optional block 980 (see FIG. 9), the worker 530 may adjust the position of the second hose anchor 562 to keep it out of the way. In block 985 (see FIG. 9), an explosion (arc flash and/or chemical) occurs. In block 990, the hose 512, which is blast-resistant, arc-flash-resistant, and fire-resistant, continues to supply fresh air into the interior 520 of the vault 414. The discharged fresh air provides sufficient breathable air to the worker 530 in the interior of the underground vault after the explosion. Thus, the hose 512 improves the worker's chances of surviving the explosion. Then, the method 900 terminates.

Computing Device

Figure 10:
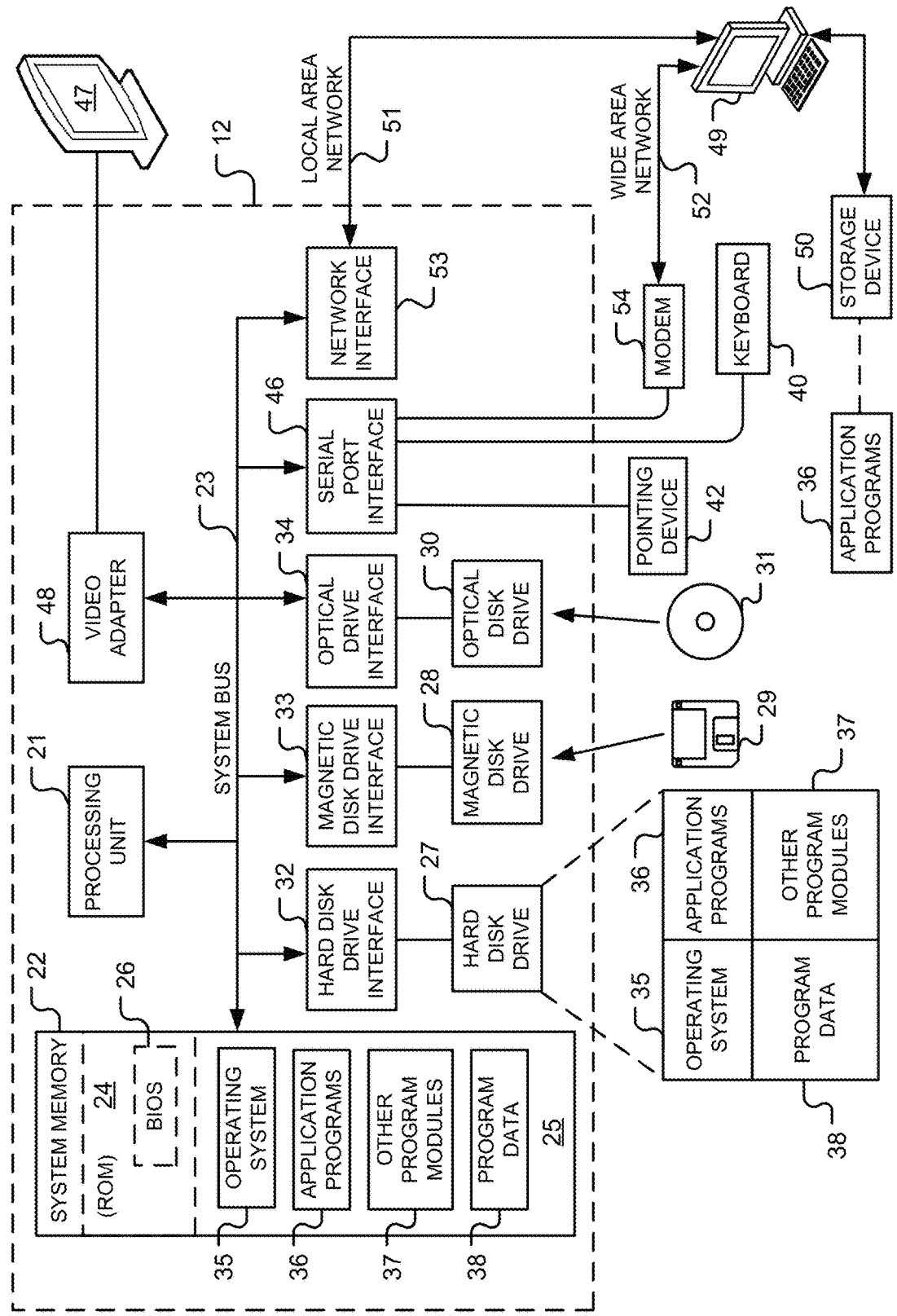
FIG. 10 is a diagram of a hardware environment and an operating environment in which the system controller of FIG. 6 may be implemented.

FIG. 10 is a diagram of hardware and an operating environment in conjunction with which implementations of the system controller 630 (see FIG. 6) may be practiced. The description of FIG. 10 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those of ordinary skill in the art will appreciate that implementations may be practiced with other computer system configurations, including hand-held devices, multi-processor systems, microprocessor-based or programmable consumer electronics, network PCs, minicomputers, mainframe computers, and the like. Implementations may also be practiced in distributed computing environments (e.g., cloud computing platforms) where tasks are performed by remote processing devices that are linked through a communications network. In a distributed computing environment, program modules may be located in both local and remote memory storage devices.

The exemplary hardware and operating environment of FIG. 10 includes a general-purpose computing device in the form of the computing device 12. The system controller 630 (see FIG. 6) may be substantially identical to the computing device 12. By way of non-limiting examples, the computing device 12 may be implemented as a laptop computer, a tablet computer, a web enabled television, a personal digital assistant, a game console, a smartphone, a mobile computing device, a cellular telephone, a desktop personal computer, and the like.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those of ordinary skill in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including the operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feed back game controller).

The input devices described above are operable to receive user input and selections. Together the input and display devices may be described as providing a user interface.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 10 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of communication and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions that when executed by one or more processors cause the one or more processors to perform all or portions of one or more of the methods described above. Such instructions may be stored on one or more non-transitory computer-readable media.

In some embodiments, the system memory 22 stores computer executable instructions that when executed by one or more processors cause the one or more processors to generate the notifications (e.g., alerts or alarms) described above. Such instructions may be stored on one or more non-transitory computer-readable media.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood with the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B, and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context.

Accordingly, the invention is not limited except as by the appended claims.

The invention claimed is:

1. A system for use with a connection extending between different first and second underground vaults, the connection comprising a wall and a terminus opening into the first underground vault, the wall defining an annulus, a cable extending through the annulus and outwardly therefrom beyond the terminus, a flow comprising one or more gases flowing through the annulus alongside the cable, the system comprising:
   a flow restrictor comprising a restriction device and a through-channel, the restriction device being configured to be installed in the annulus alongside the cable and to restrict the flow through the annulus, the through-channel being configured to allow a concentrated flow of the one or more gases to flow therethrough;
   a perturbation detector configured to detect a value of a property of the concentrated flow and to transmit a signal encoding information based on the value; and
   a system controller configured to receive the signal, use the signal to determine whether a fire is occurring or has occurred, and alert a user when the system controller determines that the fire is occurring or has occurred.

2. The system of claim 1, wherein the property is a concentration of at least one of the one or more gases.

3. The system of claim 2, wherein the perturbation detector is positioned at or near the terminus and the concentration of the at least one gas is measured in-line with the concentrated flow.

4. The system of claim 2, wherein the perturbation detector is positioned remotely with respect to the terminus and the concentration of the at least one gas is measured remotely.

5. The system of claim 1, wherein the property is a temperature of at least one of the one or more gases.

6. The system of claim 1, wherein the perturbation detector is configured to detect a magnitude of a current flowing through the cable and the signal encodes current information based on the magnitude.

7. The system of claim 6, wherein the perturbation detector comprises a first sensor configured to detect the magnitude of the current flowing through the cable and a second sensor configured to detect the value of the property.

8. The system of claim 1, wherein the property is a flow vector of the concentrated flow.

9. The system of claim 8, wherein the flow vector comprises at least one of a direction and a flow rate.

10. The system of claim 1 for use with the concentrated flow comprising particulates, wherein the property is a concentration of the particulates.

11. The system of claim 10, wherein the perturbation detector is positioned at or near the terminus and the concentration of the particulates is measured in-line with the concentrated flow.

12. The system of claim 10, wherein the perturbation detector is positioned remotely with respect to the terminus and the concentration of the particulates is measured remotely.

13. The system of claim 10, wherein the concentration of the particulates is detected by the perturbation detector using at least one of deposition or filtration.

14. A method comprising:
   obtaining, by a system controller, an estimated temperature of a cable within an annulus of a connection to an underground vault, the connection having a terminus and a flow restrictor installed at or near the terminus, the flow restrictor comprising an open-ended through-channel interconnecting the annulus of the connection with the underground vault;
   obtaining, by the system controller, a channel temperature inside the open-ended through-channel;
   determining, by the system controller, an exothermic event is likely occurring when the channel temperature is greater than the estimated temperature by more than a threshold amount; and
   alerting, by the system controller, a user when the system controller determines the exothermic event is likely occurring.

15. The method of claim 14, further comprising:
   installing the flow restrictor at or near the terminus with the open-ended through-channel interconnecting the annulus of the connection with the underground vault.

16. A method for use with an annulus of a connection interconnecting first and second underground vaults, the connection having a first terminus and a first flow restrictor installed at or near the first terminus, the first flow restrictor comprising a first open-ended through-channel interconnecting the annulus of the connection with the first underground vault, the connection having a second terminus and a second flow restrictor installed at or near the second terminus, the second flow restrictor comprising a second open-ended through-channel interconnecting the annulus with the second underground vault, the method comprising:
   obtaining, by a system controller, a first flow direction of one or more gases flowing inside the first open-ended through-channel;
   obtaining, by the system controller, a second flow direction of one or more gases flowing inside the second open-ended through-channel;
   determining, by the system controller, a gas-creating-event is occurring in the annulus of the connection when the first flow direction is toward the first underground vault and the second flow direction is toward the second underground vault; and
   alerting, by the system controller, a user when the system controller determines the gas-creating-event is occurring in the annulus of the connection.

17. The method of claim 16, further comprising:
   obtaining, by the system controller, an estimated temperature of a cable within the annulus of the connection;
   obtaining, by the system controller, a first channel temperature inside the first open-ended through-channel;
   determining, by the system controller, the gas-creating-event is an exothermic event when the first channel temperature is greater than the estimated temperature by more than a threshold amount; and
   informing, by the system controller, the user that the exothermic event is occurring when the system controller determines the gas-creating-event is the exothermic event.

18. The method of claim 16, further comprising:
   installing the first flow restrictor at or near the first terminus with the first open-ended through-channel interconnecting the annulus of the connection with the first underground vault; and
   installing the second flow restrictor installed at or near the second terminus with the second open-ended through-channel interconnecting the annulus with the second underground vault.

* * * * *